United States Patent [19]
Adell

[11] Patent Number: 4,731,018
[45] Date of Patent: Mar. 15, 1988

[54] ORTHODONTIC ARCH WIRES

[75] Inventor: Loren S. Adell, Dallas, Tex.

[73] Assignee: Trident Laboratories, Inc., Sunnyvale, Tex.

[21] Appl. No.: 946,976

[22] Filed: Dec. 29, 1986

[51] Int. Cl.⁴ .............................................. A61C 3/00
[52] U.S. Cl. ...................................... 433/20; 427/119
[58] Field of Search .................. 433/20; 427/119, 117

[56] References Cited

U.S. PATENT DOCUMENTS

| Re. 30,593 | 4/1981 | Wallshein | 433/20 |
|---|---|---|---|
| 678,453 | 7/1901 | Angle | 433/20 |
| 1,849,843 | 3/1932 | Levin | 433/20 |
| 2,821,020 | 1/1958 | Brusse | 433/20 |
| 3,043,007 | 7/1962 | Wallshein | 433/20 |
| 3,504,438 | 4/1970 | Wittman et al. | 433/20 |
| 3,725,230 | 4/1973 | Bahder et al. | 427/119 |
| 4,050,156 | 9/1977 | Chasanoff et al. | 433/20 |
| 4,585,414 | 4/1986 | Kottemann | 433/20 |

*Primary Examiner*—John J. Wilson
*Attorney, Agent, or Firm*—Rhodes and Boller

[57] ABSTRACT

Various embodiments of orthodontic arch wires are disclosed. These embodiments comprise a metal part and a plastic part arranged so that the metal part faces teeth of the arch while the plastic faces labially. The arch wire is formed by an extrusion process wherein wire is extruded to a desired cross sectional shape and plastic is then extruded onto the metal. Various embodiments are configured for different cross sectional features. By making the plastic of a coloration matching the individual's teeth, an aesthetic benefit is obtained.

15 Claims, 14 Drawing Figures

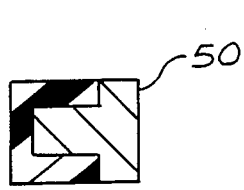
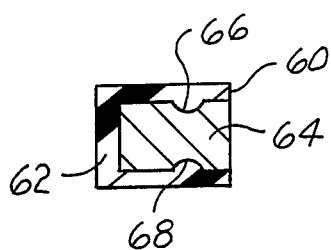
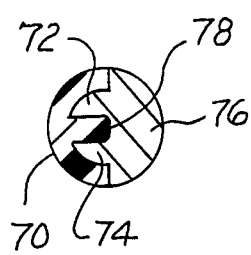
FIG. 5　　　　FIG. 6　　　　FIG. 7
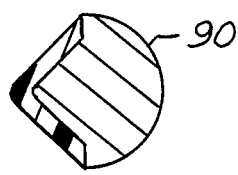
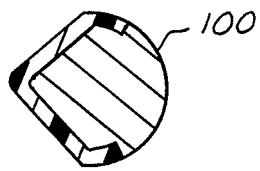
FIG. 9　　　　FIG. 10
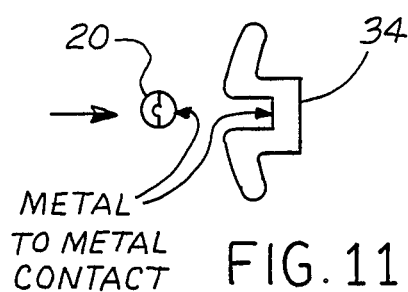
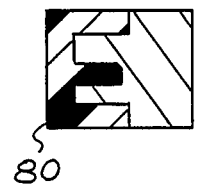
METAL
TO METAL
CONTACT　FIG. 11　　　　FIG. 8
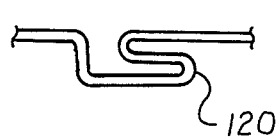
FIG. 12　　　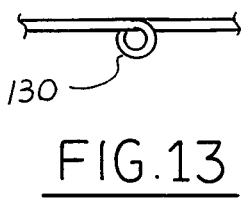　　　FIG. 14
FIG. 13

ORTHODONTIC ARCH WIRES

BACKGROUND AND SUMMARY OF THE INVENTION

This invention relates to new and useful improvements in orthodontic arch wires.

Arch wires are commonly used in orthodontic procedures in cooperative association with other components, typically brackets and buccal tubes. An arch wire is disposed on the labial side of the arch, and when connected to brackets and tubes on teeth of the arch, it serves to develop corrective forces for performing tooth movement.

Typical arch wires are a high quality stainless steel. They have either a circular transverse cross section or a rectangular transverse cross section.

Typical usage of metallic orthodontic components renders their presence apparent to others in the individual wearer's every-day activities.

In order to make orthodontic appliances more aesthetically pleasing, efforts have been made to render them less noticeable. An example of this is contained in U.S. Pat. No. 4,302,532 in which translucent plastic brackets are disclosed. The arch wire, however, has continued to be stainless steel wire and therefore, the use of plastic brackets does not provide a complete aesthetic solution. It is believed that a plastic arch wire would be generally incapable of performing orthodontic treatment procedures in the same manner as a stainless steel equivalent. An example of a plastic arch wire is shown in U.S. Pat. No. 4,585,414. It is said to possess substantially greater flexibility and resilliency than a stainless steel arch wire of the same diameter, thereby confirming the foregoing suspicisions about its equivalence to stainless steel.

The present invention relates to new and improved forms of orthodontic arch wires which possess the force tranmitting and physical performance characteristics of conventional stainless steel arch wires yet, which can also be rendered aesthetically pleasing so that the presence of the arch wire is much less noticeable than in the case of a conventional stainless steel arch wire.

Briefly, the present invention in its generic aspect comprises the selective coating of a metal arch wire with an outer covering of a non-metallic material, such as plastic, by a co-extrusion process such that the labial side of the arch wire is covered by non-metallic material which is colored to match the individual's teeth thereby rendering the presence of the arch wire much less noticeable than would be the case where the arch wire is entirely stainless steel, yet the plastic does not encapsulate the full transverse cross section of the arch wire but rather leaves that portion of the arch wire which bears against the brackets free of non-metallic material so that the steel wire itself bears against the brackets.

Further aspects of the invention relate to particular details of the transverse cross sections and a number of embodiments of such cross sections are disclosed. As will be seen, these various cross sections have particular features which are beneficial and which provide further enhancements to the manufacture and effectiveness of the arch wires.

In addition to the improved aesthetic benefit attainable with the invention and the functional benefit of metal-to-metal contact between the arch wire and brackets, there is a further functional benefit in that the inclusion of the non-metallic material on the metal of the arch wire can in certain cases provide a protection to the mouth of the individual wearer. In this regard, a commercially available product known as the "Soft Sleeve" is used to provide protection against an arch wire causing irritation to the mouth of the individual wearer. The "Soft Sleeve" is a separate piece of cylindrical tubing which is inserted onto an arch wire to a desired location of placement. It is often used incidental to a tooth extraction.

The present invention can perform the same function as the "Soft Sleeve" but without the need to have a separate sleeve inserted onto the arch wire because the arch wire of the present invention inherently contains non-metallic material on those portions of the arch wire which might in certain individuals induce irritation in adjacent soft tissue. Moreover, unlike both the "Soft Sleeve" and the plastic arch wire of U.S. Pat. No. 4,585,414, the present ach wire is capable of formation into commonly used orthodontic loops and bends.

The foregoing features, advantages and benefits of the invention, along with additional ones, will be seen in the ensuing description and claims which should be considered in conjunction with the accompanying drawings. The drawings disclose a preferred embodiment of the invention according to the best mode contemplated at the present time in carrying out the invention.

BRIEF DESCRIPTION OF THE DRAWINGS

FIG. 5–10 are views similar to FIGS. 2 and 3 illustrating further embodiments of the invention.

FIG. 11 is a view illustrating usage of the arch wire of FIG. 2 with a bracket.

FIGS. 12–14 are views of usage of the arch wire in forming certain representative orthodontic loops and bends.

DESCRIPTION OF THE PREFERRED EMBODIMENT

Figure 1:
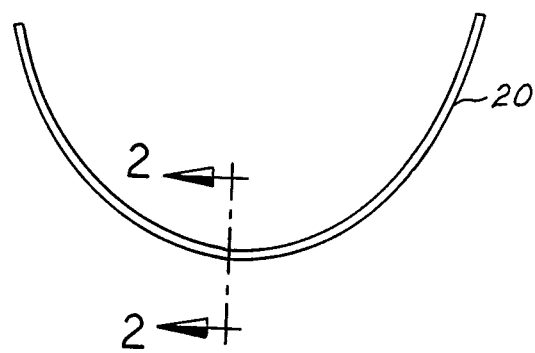
FIG. 1 is a plan view of an arch wire embodying principles of the present invention.
Figure 2:
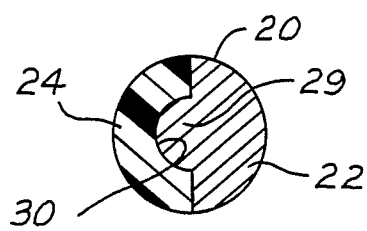
FIG. 2 is an enlarged transverse cross sectional view taken in the direction of arrows 2—2 in FIG. 1.

FIGS. 1 and 2 illustrate an arch wire 20 embodying principles of the present invention. As shown in FIG. 1, the arch wire has a shape corresponding generally to the shape of the arch to which it is to be applied. The ach wire, in orthodontic use, is cooperatively associated with additional orthodontic components such as brackets and tubes and secured to them in conventional ways so that corrective forces for performing tooth movement are transmitted via the arch wire to teeth of the arch in accordance with the treatment procedure prescribed by the attending professional.

The arch wire 20 comprises two parts: one, a metal part 22, and two, a non-metallic part 24 which is preferably plastic or equivalent material.

Figure 4:
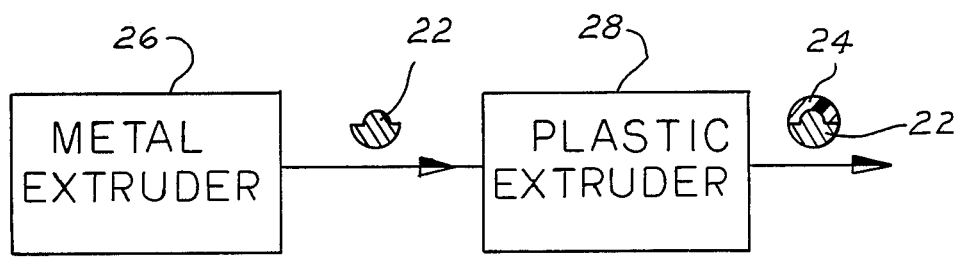
FIG. 4 is a schematic diagram illlustrating the process for fabricating an arch wire according to the present invention.

Referring now to FIG. 4, the preferred process for fabricating arch wire 20 comprises extruding metal to the desired transverse cross sectional shape for part 22 by means of a metal extruder 26. The formed metal cross section is then conducted through a plastic extruder 28 which serves to extrude the plastic material 24 onto the metal part 22. The resultant cross section at the conclusion of the extrusion operations corresponds to that portrayed in FIG. 2.

The overall cross sectional shape of arch wire 20 is circular. The two parts 22 and 24 are each essentially semi-circular but on the diameter of the metal part 24 is a semi-circular protuberance or bead 29 which is concentric with the center of the part. Correspondingly, the plastic part has a semi-circular indentation or recess 30 which fits onto protuberance 29.

With the use of the extrusion process, the plastic becomes intimately bonded to the metal so that a unitary structure results. In this regard, appropriate treatment procedures may be used to secure the desired bonding between the two materials, including the use of adhesive as required.

In orthodontic use, the metal part of the arch wire faces the teeth of the arch for cooperation with conventional brackets. This is shown in FIG. 11 where the bracket is designated 34. The plastic part faces labially so that the appearance which is presented by the arch wire in use is that of the plastic part. By making the plastic part of a coloration which matches the teeth, essentially no metal of the arch wire is visable, and the arch wire blends with the color of the teeth so that an aesthetic benefit is obtained.

Moreover, the arch wire has functional benefits. One, by having the plastic part only partially surrounding the metal, the metal itself can be disposed against the brackets with which the arch wire is cooperatively associated whereby metal-to-metal contact results. Two, the presence of the plastic material to the labial side of the arch wire can serve to alleviate sources of irritation which might be induced by metal wire contact with soft tissue.

The process depicted in FIG. 4 comprises a continuous exrusion of metal and plastic along the line. Subsequently, the individual wires are cut to length and formed to the appropriate arch shape. Because of the ability achieved in the bonding of the plastic to the metal, the plastic can tolerate the formation into the shape of the arch wire so that the cross section remains intact throughout the extent of the arch wire. Moreover, the arch wire possesses the ability to be cooperatively associated with brackets and tubes and to exert the forces which are required for orthodontic treatment because the major extent of the cross section is left substantially in tact. Stated another way, the arch wire metal is shaped to receive the plastic as an inlay without serious derogation of the mechanical bending and force-transmitting properties which the metal would exhibit absent the recessing which is imparted to it for receiving the plastic inlay.

Figure 3:
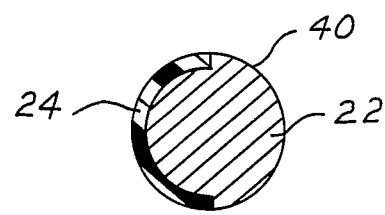
FIG. 3 is a view similar to FIG. 2 illustrating an alternate embodiment.

The embodiment 40 depicted in FIG. 3 is essentially like that in FIG. 2 but with different proportions. Here the plastic is more in the form of a thinner inlay which is inlaid into the semi-circular recess extending around the outside of the arch wire. Arch wire 40 will possess substantially the same characteristics as if the entire arch wire were of circular metal because only a relatively shallow recess of semi-circular shape is formed for the receipt of plastic. In arch wire 20 the characteristics will be somewhat different because of the larger proportion of plastic versus metal in the cross section, but the combined mechanical effect of protrusion 28 from the main semi-circular metal body in both Figs. results in labial-lingual bending resistance which at least approximates that which would exist in a full circular cross section of metal.

Arch wires of non-circular shapes are also contemplated as depicted by the embodiment 50 of FIG. 5 which illustrates a construction which is in certain respects analogous to that of FIG. 2 and 4. The rounded semi-circular shapes of FIGS. 2 and 4 are in effect transformed into square or rectangular shapes. The metal part has a T-shape with the base of the T facing labially. The plastic part is U-shaped and fits onto the base of the T. The amount of plastic versus metal also affects the characteristics of the arch wire, but it has a reasonable approximation to a square or rectangular metal arch wire of the same overall cross section. The extrusion process for fabricating this is the same as that used in FIG. 3, but with the appreciation that the shapes are different.

FIG. 6 illustrates an embodiment of arch wire 60 which is also of an overall rectangular shape but with certain differences from the embodiment of FIG. 6, particularly the greater extent of plastic. The plastic 62 covers the labial, the top, nd the bottom surfaces of the metal 64 and is inlaid into channels 66, 68 formed in the top and bottom surfaces of the metal as shown.

FIG. 7 illustrates an arch wire 70 which is similar to the embodiment of FIG. 3, but with two protuberances 72, 74 provided in the metal part 76 on opposite sides of a recess 78.

FIG. 8 illustrates an embodiment 80 which may be considered as a rectangular version of embodiment 70.

The embodiments 90, 100 shown in FIGS. 9, and 10 are half of a circular cross section combined with half of a rectangular cross section.

Any of various bio-compatible plastics (PVC material, vinyl, elasticized acrylic) are suitable for use in the arch wire.

FIG. 11 illustrates one of the advantages of the invention. The drawing figure is a cross section illustrating the manner in which the arch wire is fitted to a bracket. Because the lingual surface of the arch wire is metal, metal-to-metal contact will result between the arch wire and bracket when the arch wire is inserted into the bracket grooves.

Another advantage of the invention is portrayed in FIGS. 12–14. As stated above, it is possible to form the wire after extrusion into the desired arch wire shape. Because of the intimate bonding which occurs beween plastic and metal in consequence of extrusion, and in view of the ability of certain plastics to elongate slightly without delamination, such bending is rendered possible. Moreover, because the body of the arch wire is mostly metal and because of the ability of the plastic to have some degree of elongation, intricate loops and bends can also be formed in the arch wire.

FIG. 12 illustrates one example, namely, a boot loop 120. FIG. 13 illustrates a single helix 130, and FIG. 14 illustrates a "T" loop 140.

With the plastic arch wire described in U.S. Pat. No. 4,585,414, the inherent flexibility would prevent the arch wire from being formed into these loops and functioning; likewise, a separate device, such as the "Soft Sleeve" referred to earlier, could not be inserted onto these loops. Therefore, the present invention is especially important when consideration is given to the need to form an arch wire into any of the conventionally known bends and loops such as the three examples described in FIGS. 12–14.

While the foregoing has described preferred embodiments of the invention, it will be appreciated the principles are applicable to other embodiments.

What is claimed is:

1. An improved orthodontic arch wire comprising in combination with one or more rigid orthodontic brackets having labially open slots into which the arch wire is received, said arch wire comprising a metallic part and a non-metallic part securely joined together, said two parts being arranged such that the metallic part faces teeth of the arch to which the arch wire is to be applied and is in direct contact with the interior of each slot, and the non-metallic part faces labially fully covering the metallic part on the labial side of the arch wire.

2. The improvement set forth in claim 1 in which the arch wire has an overall circular transverse cross section.

3. The improvement set forth in claim 2 in which one part has an outer surface of semi-circular extent and a centrally disposed protuberance, and the other part has a semi-circular outer surface and a centrally disposed recess which receives the semi-circular protuberance of the one part.

4. The improvement set forth in claim 3 in which the protuberance is in the metallic part.

5. The improvement set forth in claim 1 in which the arch wire has an overall rectangular shape.

6. The improvement set forth in claim 5 in which the metallic part has a general T-shape in which the base of the T faces labially and in which the non-metallic part is a U-shape which fits onto the labially projecting base of the T.

7. The improvement set forth in claim 5 including grooves which run straight along the length of the arch wire in the outer surface of the metallic part underlying portions of the non-metallic part and said non-metallic part includes non-metallic material filling said grooves.

8. The improvement set forth in claim 1 in which the arch wire has a combined semi-rectangular and semi-circular shape having the semi-rectangular shape on the labial side and the semi-circular shape on the side which faces the arch and is in direct contact with the interior of each such slot.

9. The improvement set forth in claim 8 in which the non-metallic part extends from the semi-rectangular portion to partially overlap the semi-circular portion.

10. The improvment set forth in claim 1 in which the overall transverse cross section of the arch wire has a circular shape and the metallic and non-metallic parts have respective non-circular shapes combining to form the overall circular shape.

11. The improvement set forth in claim 1 in which the overall transverse cross section of the arch wire has a rectangular shape and the metallic and non-metallic parts have respective non-rectangular shapes combining to form the overall rectangular shape.

12. The method of making an orthodontic arch wire which comprises extruding metal wire to a desired transverse cross sectional shape; extruding a non-metallic material onto the metal wire of desired transverse cross sectional shape such that the non-metallic material covers a selected portion of the surface of the cross section of the metal less than the entire surface of the cross section thereby leaving exposed metal along another selected portion of the surface of the cross section; and forming the resulting product into the shape of an arch wire having concave and convex sides such that the exposed metal is along the concave side of the arch wire and the non-metallic material is along the convex side.

13. The method set forth in claim 12 in which the non-metallic material comprises plastic.

14. An improved orthodontic arch wire comprising a metallic part and a non-metallic part securely joined together, said two parts being arranged such that the metallic part faces teeth of the arch to which the arch wire is to be applied and the non-metallic part faces labially, said arch wire having an overall rectangular shape in transverse cross section in which the metallic part has a general T shape in which the base of the T faces labially and in which the non-metallic part is a U-shape which fits onto the labially projecting base of the T.

15. An improved orthodontic arch wire which comprises a metallic part and a non-metallic part securely joined together, said metallic part having outer and inner peripheral portions, said outer peripheral portion of the metallic part being disposed labially when the arch wire is applied to an arch, and said non-metallic part covering the entire outer peripheral portion of the metallic part, but leaving at least some of the inner peripheral portion exposed, said metallic and non-metallic parts having complementary transverse cross sections cooperatively forming the arc wire's cross section, but the transverse cross section of the non-metallic part by itself being different from the transverse cross section of the metallic part by itself.

* * * * *